United States Patent [19]

Jullien

[11] Patent Number: 5,015,234
[45] Date of Patent: May 14, 1991

[54] SYRINGE GUARD APPARATUS

[76] Inventor: Robert G. Jullien, 2904 Graham Rd., Falls Church, Va. 22042

[21] Appl. No.: 360,585

[22] Filed: Jun. 2, 1989

[51] Int. Cl.⁵ .................................................. A61M 5/00
[52] U.S. Cl. ..................................... 604/110; 604/192
[58] Field of Search ............... 604/198, 110, 187, 192, 604/263

[56] References Cited

FOREIGN PATENT DOCUMENTS 2202747 10/1988 United Kingdom ................ 604/192

Primary Examiner—John D. Yasko
Attorney, Agent, or Firm—Longacre & White

[57] ABSTRACT

A needle guard for use with a syringe barrel including a mechanism for selectively enabling and not enabling passage of a needle through the end of the guard. Further, the guard includes an end closure for permanently closing a needle aperture therein and positively destroying the needle upon telescopically moving the guard and syringe barrel to a respectively retracted position.

8 Claims, 10 Drawing Sheets

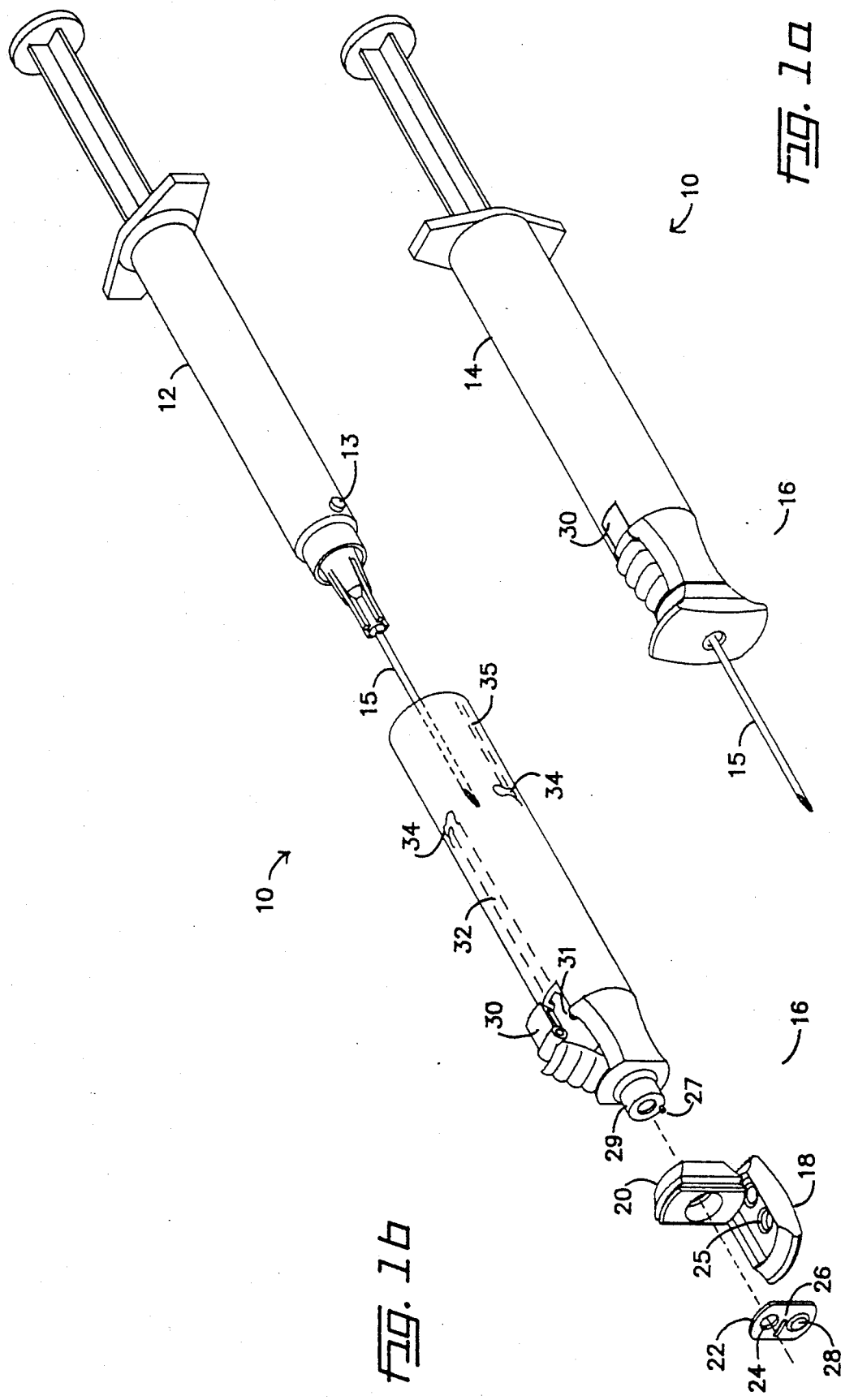

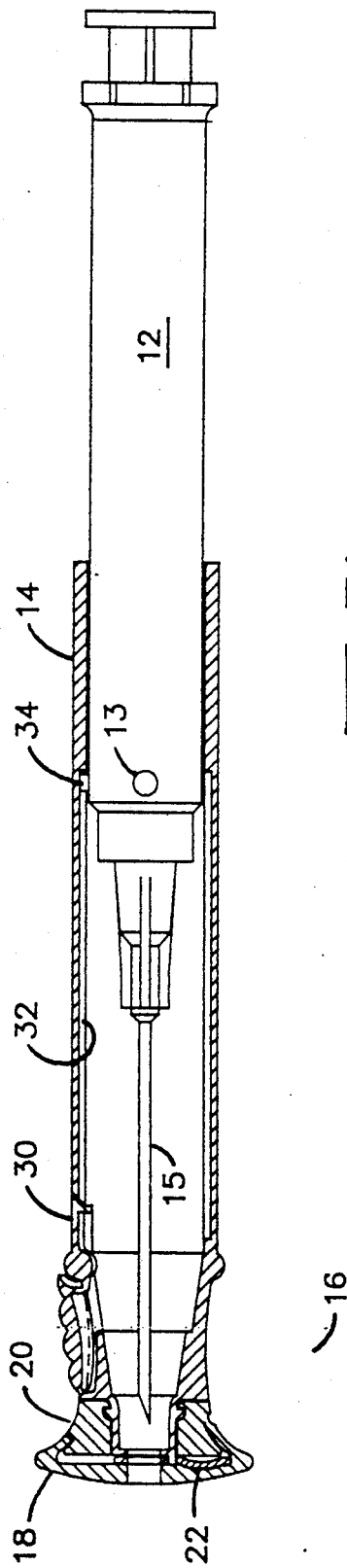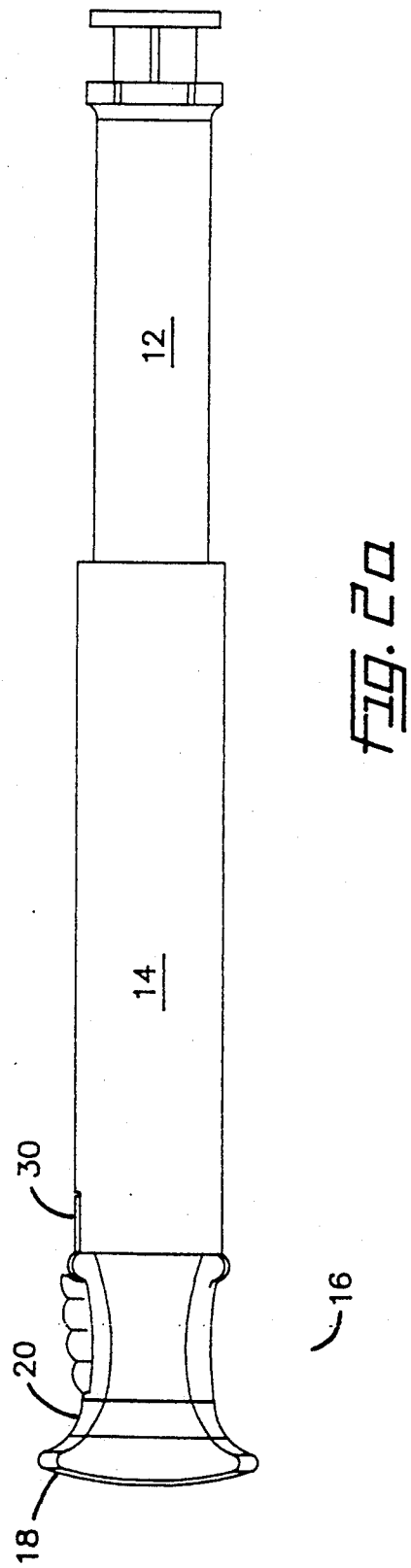

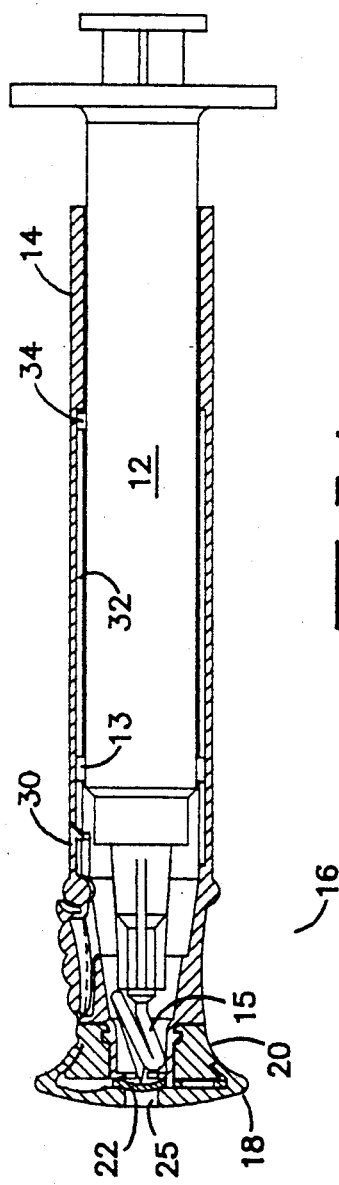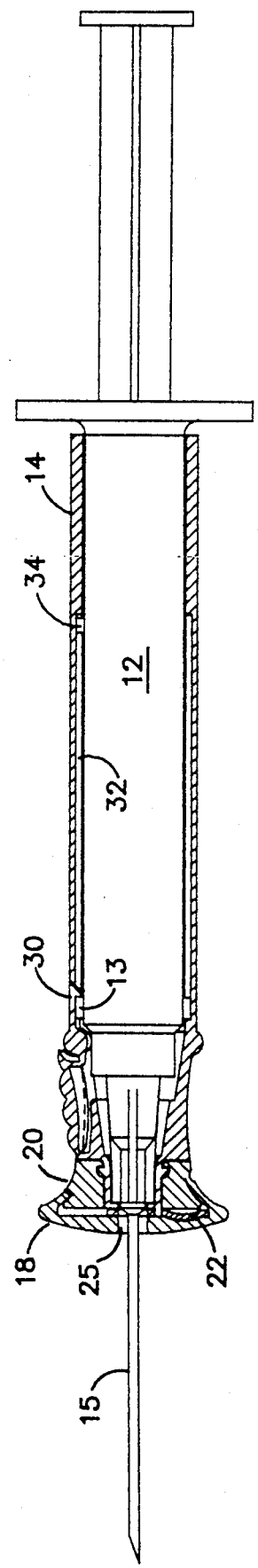

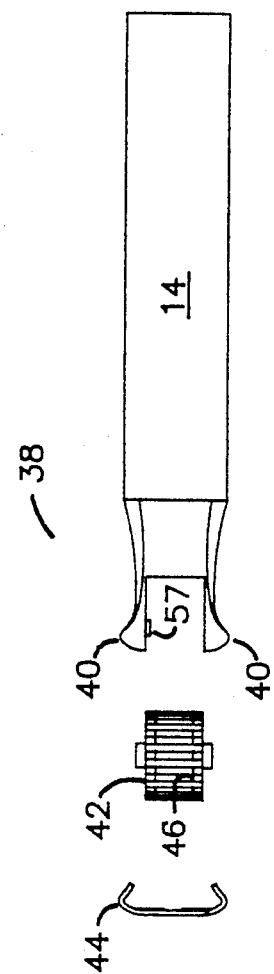
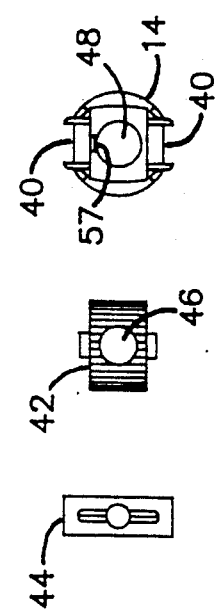
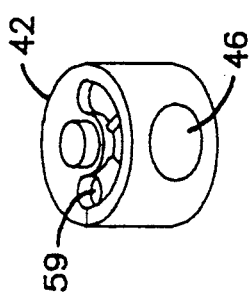

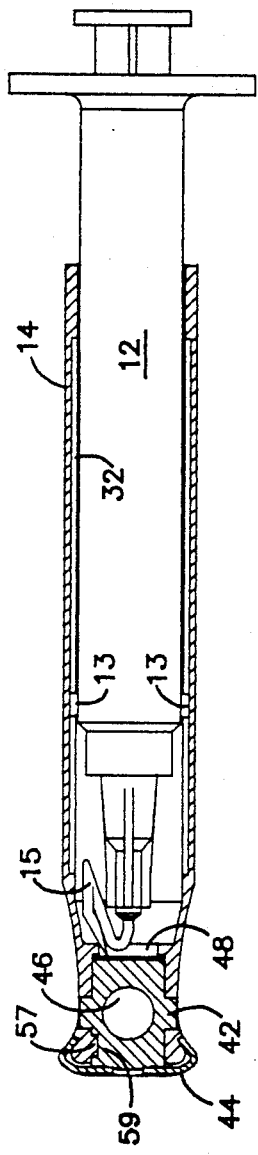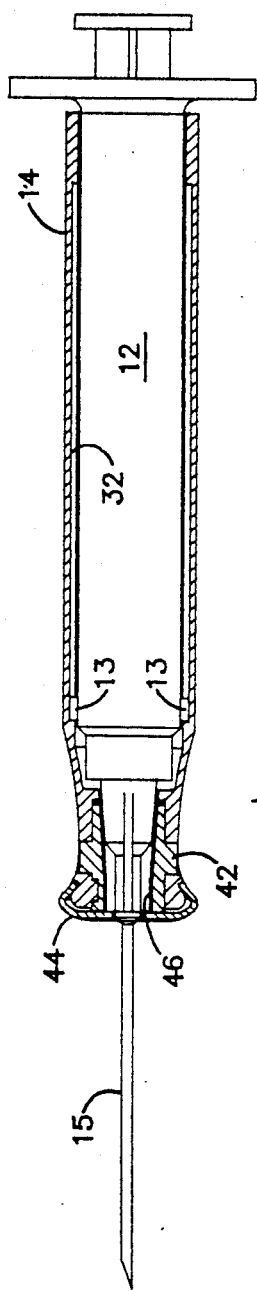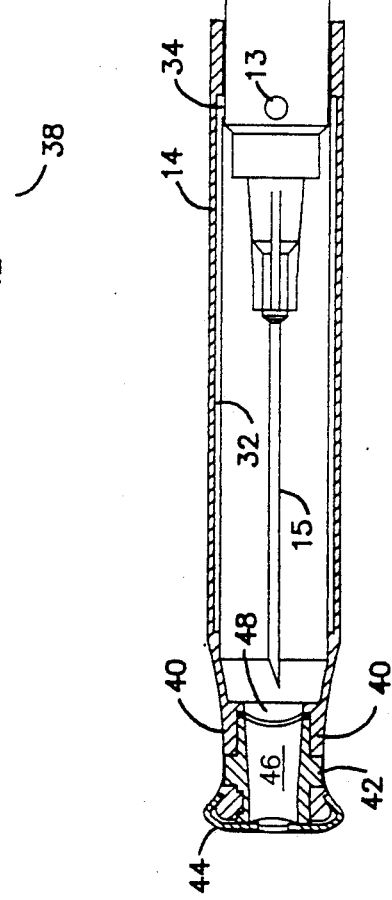

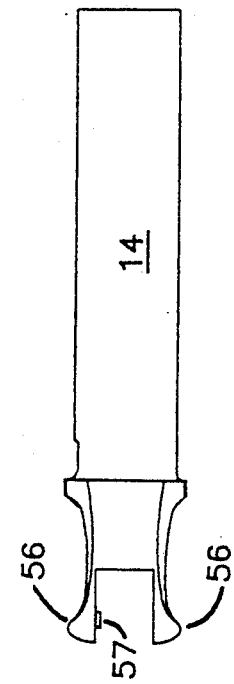
Fig. 5b
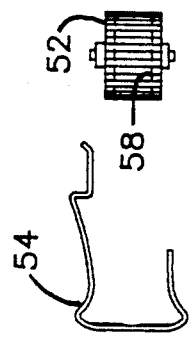
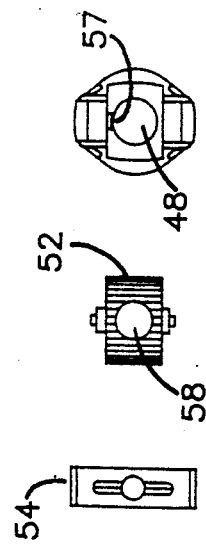
Fig. 5a

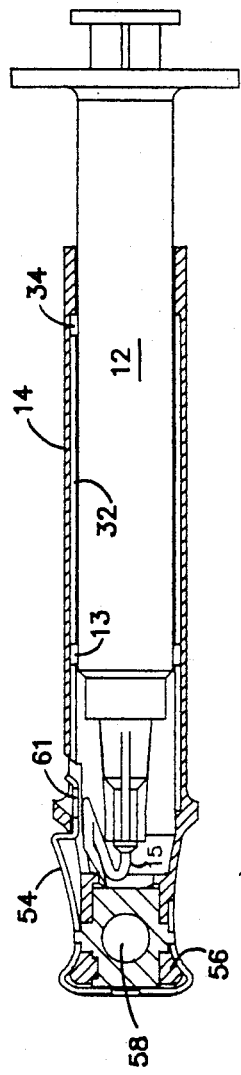
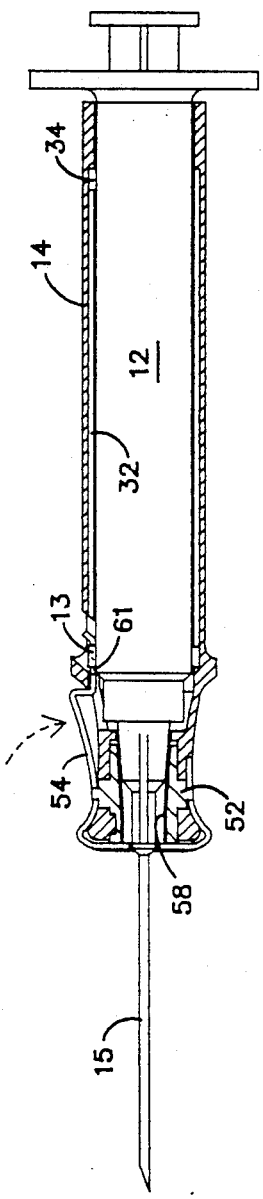
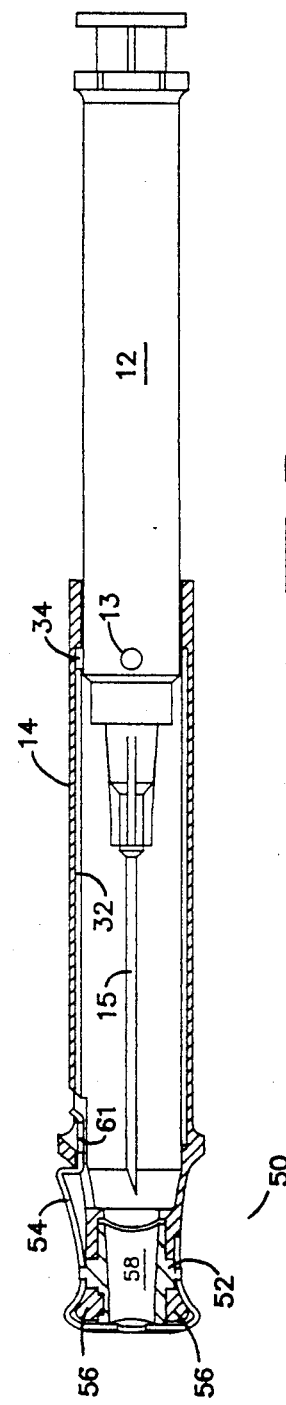

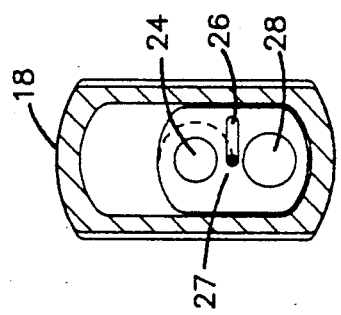
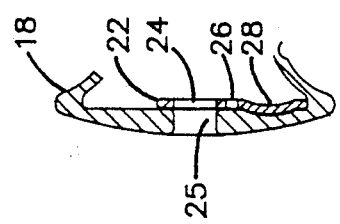
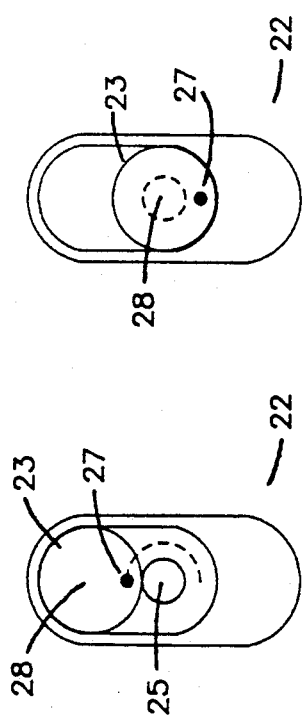
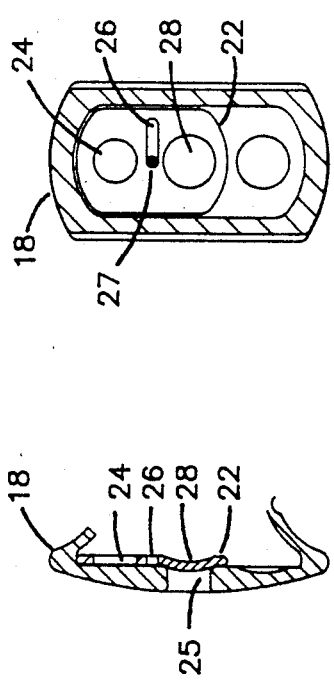

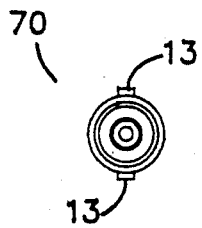
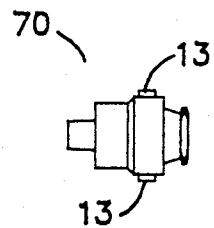
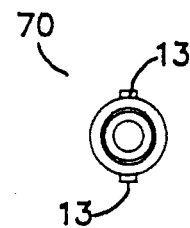
fig. 9a  fig. 9b  fig. 9c
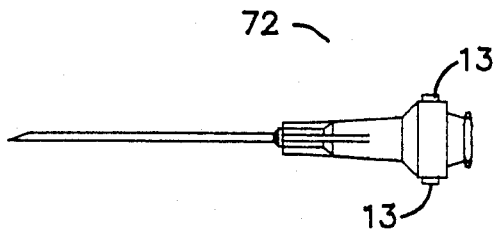
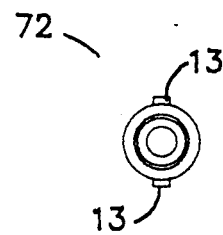
fig. 10a  fig. 10b
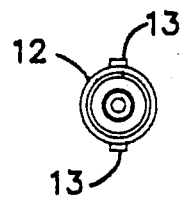
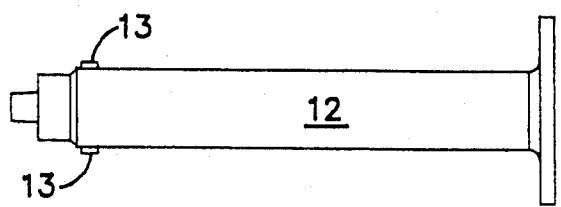
fig. 11a  fig. 11b

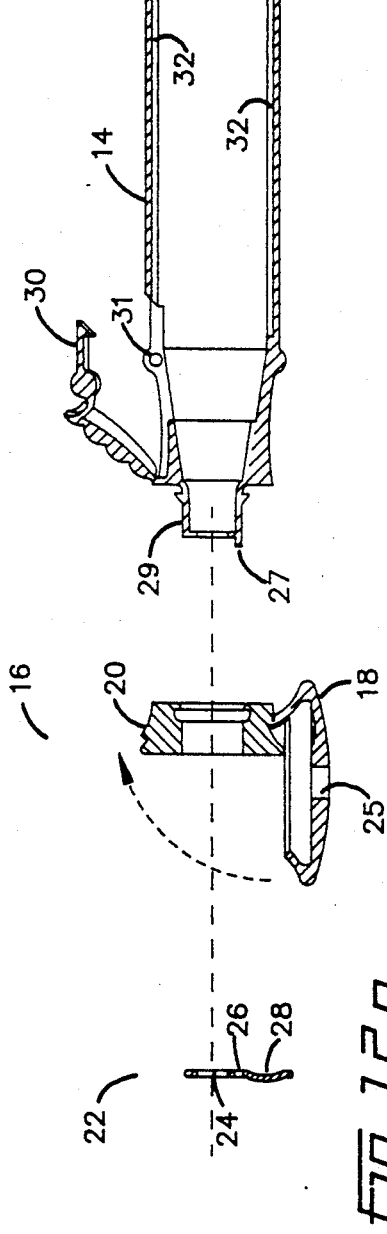

SYRINGE GUARD APPARATUS

FIELD OF THE INVENTION

The present invention relates to the field of medical equipment. Specifically, the present invention relates to an apparatus for preventing unintended contact of a needle with foreign objects. Particularly, when an injection is to be or has been given, or a sample been withdrawn, with respect to a patient, it is a necessity that the needle does not foul an attendant person or object and perhaps pass bloodborne or other fluidborne pathogens.

BACKGROUND OF THE INVENTION

Discoveries in medical science have long indicated that certain diseases are passed through unintended contact with contaminated needles. Specifically, blood to blood contact, or internal fluid to internal fluid contact, can spread diseases and germs which otherwise cannot be transmitted. To avoid such unintended transmission of pathogens by contaminated needles, particularly for medical professionals, several proposals have been advanced.

The most recent of these proposals has to do with the widely available needle, syringe, and needle cap combination. Specifically, certain governmental agencies are in the process of promulgating guidelines which outline several procedural methods of dealing with the inadvertent spread of infection through contaminated needles. While these procedural suggestions are useful, if they are unobserved, or a participant unavoidably fouls a needle against their person, the disease is none-the-less transmitted.

To address human fallibility with respect to following procedures, several needle guard type apparatus have been suggested. Specifically, guards which telescopically cover the syringe barrel and needle portion have been proposed. These guards may optionally include latching mechanisms at either end of the guard so as to hold the guard in a particular position with respect to the needle and syringe combination. Further, many of the guards are also proposed as permanent disposal devices for the needle so that if medical waste is improperly disposed, the risk of a contaminated needle subsequently fouling an individual's person is reduced.

Examples of such prior art guard apparatus can be found in U.S Pat. Nos. 4,731,059, 4,643,199, 4,425,120, 4,770,655, 4,710,170, 4,728,320, 4,702,738, 4,801,295, and 4,634,428. While these prior art devices provide guards for covering or shielding a needle and syringe combination, they are uniformly cumbersome and complex. As such, the devices are not in wide spread use for a variety of reasons.

SUMMARY OF THE INVENTION

It is an object of the present invention to provide a user friendly and cost efficient apparatus for shielding a needle and syringe combination from inadvertent fouling. The guard assembly according to the present invention is a simple three piece unit, and can optionally include an easily operated latching mechanism for manipulating the guard between an extended and retracted position. Further, the present invention has a simplified needle disposal technique whereby the needle is positively destroyed and contained within the locked guard and syringe barrel combination.

The present invention includes several embodiments, either with or without a latching mechanism for maintaining the guard in a retracted position. Further, the several embodiments herein disclosed include adapter mechanisms for standard syringe barrels so that the present invention may be used with the present stock of existing syringes.

Additional features and advantages of the present invention will become apparent upon the reading of the following description in association with the drawings and appended claims, which form a part thereof.

BRIEF DESCRIPTION OF THE DRAWINGS

FIG. 1(a) is an isometric view of a guard and syringe assembly according to the present invention.

FIG. 1(b) is an exploded isometric view of a guard and syringe combination according t the present invention.

FIGS. 2a-d are plan and sectional views of a guard and syringe assembly according to the present invention of the embodiment shown in FIG. 1.

FIGS. 3a and b are exploded front and elevational views of a guard and end-piece combination according to the present invention without an end-latch.

FIG. 3c is an isometric view of a thumb wheel according to the present invention.

FIG. 4a-c are sectional views of a guard and syringe combination according to the present invention of the embodiment disclosed in FIG. 3.

FIGS. 5a and b are exploded front and elevational views of a guard according to the present invention including a latching mechanism.

FIGS. 6a-c comprise sectional views of a guard and syringe combination of the embodiment shown in FIG. 5.

FIGS. 7a-d are end and sectional views of a moving plate assembly incorporated in the guard of the present invention of the embodiment shown in FIG. 1.

FIGS. 8a-b are end views of a moving plate assembly according to the present invention of an alternative end piece embodiment for use in the guard embodiment shown in FIG. 1.

FIGS. 9a-c are end and side views of an adapter according to the present invention.

FIGS. 10a-b are side and end views of a combination needle and adapter according to the present invention.

FIGS. 11a-b are end and side views of a syringe barrel according to the present invention.

FIGS. 12a-c are longitudinal sections of a guard assembly according to the present invention.

FIGS. 13a-c are perpendicular sectional views of the guard assembly shown in FIGS. 12a-c.

DETAILED DESCRIPTION OF THE PREFERRED EMBODIMENT

A guard and syringe combination is shown in FIGS. 1a and 1b and is generally designated by numeral 10. The guard and syringe combination includes a syringe barrel portion 12, a guard 14, and an end-piece 16. The syringe barrel is of a commercially available variety, and is composed of molded plastic and accommodates a plunger for injecting or withdrawing fluid through the needle 15.

The guard portion 14 forms a cylindrical barrel open at one end and closed at the other. The open end telescopes over the forward end of a syringe barrel so as to enclose the needle attached to the forward end of the syringe barrel. To aid in the alignment and guidance of the syringe barrel within the guard, the guard is equipped with syringe removal slots 35 and interference protrusions 17. The syringe removal slots 35 engage and guide tabs 13 on the syringe barrel into locking slots 34 (discussed hereinafter), thereby securely engaging the syringe and guard assembly. The interference protrusions 17 engage and slide along the barrel of the syringe so as to aid in aligning the syringe and guard longitudinally. This precise alignment between the guard and syringe barrel aids in assuring accurate alignment of needle 15 within the guard 14.

The guard 14 includes an end-piece 16 attached to the substantially closed end of the guard. The end-piece comprises a mechanism for alternately opening a passage aperture, and closing this passage aperture, through which the needle passes for use.

In the embodiment shown in FIG. 1, guard 14 includes an end-piece 16. The end-piece is comprised of a cap-piece 18 and a gripping band 20. Located between the cap-piece 18 and the gripping band 20 is a sliding plate member 22. This plate member may take on several designs as will be discussed later.

The end-piece 16 is rotatably engaged on the end of guard 14 about cylinder 29. Cylinder 29 has an aperture passing through the center thereof (unnumbered), which aperture provides a throughway for the needle to pass from the syringe barrel 12.

Pin 27 extends from a forward end of cylinder 29 and engages slot 26 in sliding plate 22. The relative movement between slot 26 and pin 27 enable sliding plate 22 to move between two positions upon rotation of end-piece 16 with respect to guard 14. Specifically, sliding plate 22 includes aperture 24 as well as impenetrable surface portion 28. By moving the sliding plate so that aperture 24 and impenetrable surface 28 alternately align with aperture 25, a user may either permit or prevent passage of a needle 15 through aperture 25 in cap-piece 18.

In this manner, a user of the guard and syringe combination according to the present invention may selectively encapsulate the needle between uses or permanently encapsulate the needle subsequent to use.

To aid in positively locating the syringe barrel 12 and guard 14 longitudinally with respect to the other, the guard is equipped with latch mechanism 30. The latch in this embodiment is comprised of a single molded plastic piece having a latching portion and a levering portion. A pivoting linking portion connects the respective latching and levering portions and enables engagement and disengagement of the latch from tab 13. The pivoting linking portion engages a raised portion of the guard by way of latch pins 31. In this manner, pressure exerted on the levering portion results in a pivoting action being imparted to the latching portion so as to raise and lower the latching portion to clear tab 13. (See FIG. 2b explained below.)

The sequence of operation of the guard and syringe combination disclosed in FIG. 1 will be explained with reference to drawing FIGS. 2a–2d.

FIG. 2a shows an elevational view of a guard and syringe assembly according to the present invention. Guard 14 telescopically envelopes the forward end of syringe barrel 12. The guard includes end piece 16 and latch 30. This Fig. shows the syringe and guard in the fully extended "as packaged" condition.

FIG. 2b shows the guard and syringe of FIG. 2a in the "as packaged" configuration, but in a partial sectional view so as to expose the working portions of the guard. The forward end of guard 14 includes latch 30 mounted thereon. The latch includes the respective latching and levering portions as previously discussed.

FIG. 2c shows the guard 14 and syringe 12 in the fully retracted position, with the latching portion of latch 30 securely engaged about tab 13. The guard 14 and syringe 12 are securely fixed in this retracted and "ready for use" position until an operator releases latch 30 and returns the guard and syringe to the fully extended position shown in FIG. 2b. Subsequent to returning the guard and syringe to this position, an operator may optionally lock tabs 13 into locking slots 34 so as to secure the guard and syringe in the fully extended position. Also, an operator may optionally close aperture 24 by relatively rotating the guard and end piece 16. In this manner, the needle is completely encapsulated within guard 14.

After an operator has disposed of or otherwise completed the utilization of the needle and syringe, the guard and syringe are placed in the fully extended position. The end piece 16 and guard are rotated so as to close aperture 24 with plate 22, and the guard and syringe are telescoped to the fully retracted position to positively destroy needle 15. This configuration is shown in FIG. 2d. In this manner, the contaminated needle is thereafter unable to foul a person or attendant object.

FIGS. 3a–c show an alternative embodiment of a guard according to the present invention. The alternative embodiment includes a guard portion 14 in combination with a particular end-piece which is cast integrally with the guard. End-piece 38 includes stirrup portions 40. Stirrups 40 extend and surround a thumb wheel 42. Thumb wheel 42 is held in position on stirrups 40 by a clip member 44. The thumb wheel 42 includes an aperture 46 which, by rotation between three positions, selectively allows passage of a needle through the end portion of guard 14. The thumb wheel is rotatable between three positions wherein the aperture 46 is aligned with the needle passing through guard 14, in a second position wherein the aperture 46 is releasably held perpendicular to the passage 48 through guard 14, or a third position wherein the aperture 46 is substantially permanently held in a position perpendicular to the passage of a needle 15.

FIG. 3c shows the thumb wheel in isometric view. This view shows the locking mechanism for the thumb wheel. Specifically, thumb wheel 42 includes a locking aperture 59 which engages locking pin 57 on stirrups 40. Hence the thumb wheel may be rotated in two directions. A first direction which allows rerotation of the thumb wheel back to a position to allow passage of needle 15, and a second direction which positively locks the thumb wheel in a blocking position for permanent disposal of the guard and syringe combination.

In this manner, the rotatable thumb wheel 42 enables a user to selectively encapsulate or allow passage of a needle through guard 14. This sequence of operation is demonstrated in FIGS. 4a–c.

FIG. 4a shows a syringe 12 installed in guard 14 including end-piece 38. FIG. 4a is a sectional view of the guard and a plan view of the syringe barrel and needle combination. In FIG. 4a, thumb wheel 42 is shown with aperture 46 in alignment with needle 15. From this configuration, a user merely rotates guard 14 and barrel 12 to an unlocked position, and moves guard 14 to a retracted position with respect to syringe barrel 12.

FIG. 4b demonstrates the guard 14 and barrel 12 in the fully retracted position. In this position, the needle 15 is exposed and may be used for either injecting or withdrawing a sample as desired.

FIG. 4c demonstrates the disposed and needle destroyed condition of the guard and barrel combination. The transition from "in use" in FIG. 4b to disposal FIG. 4c is as follows. Once a sample has been withdrawn or injected and the syringe is otherwise ready for disposal, the syringe and guard combination are returned to the fully extended position as demonstrated in FIG. 4a. Once in this position, the thumb wheel 42 is rotated 90 degrees so that aperture 46 is no longer aligned with needle 15 and locking aperture 59 and locking pins 57 engage. The guard and syringe barrel combination is then moved to the fully retracted position crushing needle 15 against the thumb wheel 42 as guard 14 and barrel 12 telescope to the retracted position. In this manner, the needle 15 is destroyed and incapsulated to the extent that the possibility of its fouling the user or a subsequent individual which encounters the syringe is significantly reduced.

Also shown in these drawing figures is the interaction of guide slots 32 and guide tabs 13. Guide tabs 13 slide along slots 32 and, in combination with locking L-slots 34 (shown in FIG. 1), provide a mechanism for latching the guard and syringe barrel in the extended position shown in FIG. 4a. (Note that the syringe barrel and guard are rotated with respect to one another such that FIG. A demonstrates the locked position.) For the syringe barrel 12 and guard member 14 to be relatively telescopically movable, the barrel and guard must be rotated with respect to one another 90 degrees so that tabs 13 disengage locking slots 34 and align with longitudinal slots 32, as shown in FIGS. 4b and 4c, and enable the guard 14 and barrel 12 to telescope with respect to one another.

FIG. 5 discloses an alternative embodiment of the thumb wheel embodiment shown in drawing FIG. 3. This embodiment of the invention includes an end-piece 50 which includes stirrups 56, thumb wheel 52 (substantially similar to thumb wheel 42), and latch 54. In this embodiment, the latch 54 includes a clip which engages guide tab 13 when the guard and syringe barrel are in the fully retracted position. Thumb wheel 52 also includes an aperture 58 which permits passage of a needle there through.

The sequence of operation of the guard and end-piece shown in FIG. 5 is demonstrated in FIGS. 6a-c. FIG. 6a shows a sectional view of guard 14 in combination with a side view of syringe barrel 12. The syringe barrel fits telescopically within the guard 14 with needle 15 protruding towards the thumb wheel 52. Thumb wheel 52 is shown aligned with needle 15 such that aperture 58 will enable passage of needle 15. The guard 14 and barrel 12 are moved to the fully retracted position shown in FIG. 6b and the syringe is ready for use.

FIG. 6b shows the interaction of clip 54 and tab 13. The clip 54 includes a locking aperture 61 on a forward tab portion of the lock. This locking aperture 61 slips over and clips on to tab 13 when the guard 14 and barrel 12 are in the fully retracted position. To release the clip, a user exerts force in the direction of the dotted arrow shown in FIG. 6b. Such force will result in a pivoting motion of a forward tab of the clip so that aperture 61 can clear tab 13 and the telescoping function of the respective guard 14 and barrel 12 is once again achieved.

The sequence of operation whereby needle 15 is destroyed is identical to that disclosed with respect to FIG. 4. Specifically, once a user is finished with the syringe and needle combination, the guard and barrel are returned to the fully extended position, thumb wheel 52 is rotated so that aperture 58 no longer aligns with the needle and the thumb wheel is in the locked position, the barrel and guard combination is then returned to the fully retracted position crushing needle 15 between the telescoping guard 14 and syringe barrel 12.

FIG. 7 discloses an embodiment of the sliding plate 22 embodiment of the present invention. Cap piece 18 includes sliding plate 22. The plate 22 includes slot 26 which engages and interacts with actuating pin 27. Upon relative rotation of the guard and end-piece, pin 27 translates plate 22 to a position so as to either align with or not align with aperture 25. In this way, aperture 25 is selectively blocked or left open so as to allow needle 15 to pass there through. When a user has determined that the syringe and needle combination should be destroyed, end piece 16 is rotated past the point necessary to position plate 22 over aperture 25. In this manner, pin 27 is sheared and no longer able to impart movement to plate 22. Hence, plate 22 is positioned so as to permanently block aperture 25. The guard and syringe barrel are then moved to the respectively retracted position so as to destroy and disable the syringe and needle combination.

FIG. 8 discloses an alternative embodiment of sliding plate 22 which may be incorporated in the end-piece of guard 14 shown in FIG. 1. The end-piece includes plate 22 which accomplishes the blocking function of the aperture for the needle 15 provided in the forward end of guard 14. The sliding plate shown in FIG. 8 is comprised of two moving parts. The plate 22 includes a circular sliding member 23 which is moved between an aperture covering position and an aperture uncovering position. Pin 27, mounted on cylinder 29, engages plate 23 and rotates and slides the plate upon relative rotation of the end-piece and guard 14 so that the plate moves from the position shown in FIGS. 8a to that shown in FIG. 8b. The open aperture 25 in the cap is irreversibly closed by this action. When the user has determined that the needle and syringe should be destroyed/disabled, the user twists the end cap and barrel to the extent necessary to position plate 23 over aperture 25. The plate is then immovably placed so as to cover aperture 25. Subsequent to placing the plate 23 in this position, the guard and barrel are moved telescopically to the fully retracted position crushing needle 15.

The above described sliding plate and end cap apparatus may be comprised of plastic or other suitable material which resists penetration of the variety of needles presently in use for medical or other purposes.

FIG. 9 shows an adapter for use with existing syringe barrel stock so as to adapt an existing syringe barrel for use with a guard according to the present invention. The adapter fits between an existing syringe and needle attachment so that a guard according to the present invention can be used there with. The particular features of the adapter which enable such usage are the inclusion of guide tabs 13 for engagement in slots 32 of guard 14.

FIG. 10 shows a needle adapter. The needle adapter 72 is equipped with guide tabs 13 which also engage slots 32 and enable the use of a guard according to the present invention in combination with a standard syringe barrel.

FIG. 11 discloses a syringe barrel for use with the present invention. The particular feature of the barrel which enables use with a guard according to the present invention is the inclusion of guide tabs 13.

FIG. 12 shows an exploded sectional elevational view of the guard 14 of the embodiment shown in FIG. 1. This Fig. shows the pivoting and connecting relationship between the respective end piece members. This Fig. also shows syringe removal slots 35.

FIG. 13 shows sectional views of the guard embodiment shown in FIG. 12 along the indicated sections, including end view FIG. 13c. FIG. 13a shows the particular location of locking slots 34 and their relationship to guide slots 32. FIG. 13b shows the location of syringe removal slots 35. FIG. 13c shows an end view of the guard 14, and discloses the location of interference protrusions 17.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

I claim:

1. An assembly adapted for injecting or drawing fluid into or from a surface, said assembly comprising:
   a barrel portion for containing fluid, said barrel being equipped with a needle on an end thereof, said needle being adapted to pass fluid contained in said barrel into or from said substrate;
   tubular guard means telescopically related to and surrounding the end of said barrel equipped with said needle, said guard means having first and second ends and being adapted to telescope along said barrel between a first extended position, and a second retracted position; and,
   end-piece means mounted on a first end of said guard means, said end-piece capable of being oriented in first and second positions, said first position allowing passage of said needle through said first end of said guard when said guard is moved to said retracted position, said second position of said end-piece means blocking passage of said needle through said first end of said guard means, and enabling positive destruction of said needle when said guard is moved to said retracted position, wherein
   said end piece comprises a rotatable insert mounted for rotation about an axis within said first end of said guard, said axis being transverse with respect to the direction of said needle, said wheel member including an aperture therethrough transverse to said axis, said aperture being approximately aligned with said needle when said rotatable insert is oriented in said first position, and not aligned with said needle when said rotatable insert is in said second position.

2. An assembly as in claim 1, wherein said end piece further comprises:
   stirrup means for rotably holding said insert.

3. An assembly as in claim 2, wherein said end piece further comprises:
   locking means for locking said end piece in said second position.

4. An assembly as in claim 1, wherein said end piece further comprises:
   slidable plate means for alternately blocking and allowing passage of said needle through said first end of said guard, said plate means slidable between said first and second positions upon rotation of said end-piece with respect to said guard.

5. An assembly as in claim 4, wherein said endpiece further comprises:
   pin means for engaging said slidable plate means and moving said slidable plate between said first and second positions upon rotation of said end-piece with respect to said guard.

6. An assembly as in claim 1, further comprising:
   latching means for selectively locking said guard and said barrel portion in either of said first extended or second retracted positions.

7. An assembly adapted for injecting or drawing fluid into or from a substrate, said assembly comprising:
   a barrel portion for containing fluid, said barrel being equipped with a needle on an end thereof, said needle being adapted to pass fluid contained in said barrel into or from said substrate;
   tubular guard means telescopically related to and surrounding the end of said barrel equipped with said needle, said guard means having first and second ends and being adapted to telescope along said barrel between a first extended position and a second retracted position; and,
   rotatable end-piece means mounted on a first end of said guard means for rotation about an axis transverse to the direction of said needle, said end-piece adapted to be rotated between first and second positions, said first position allowing passage of said needle through said first end of said guard when said guard is moved to said retracted position, said second position of said end-piece means blocking passage of said needle through said first end of said guard means, and enabling positive destruction of said needle when said guard is moved to said retracted position.

8. An assembly as in claim 7, wherein said end piece further comprises:
   rotatable insert means rotatably held in said end piece, and
   stirrup means for rotatably holding said insert.

* * * * *